Figures 7, 8:
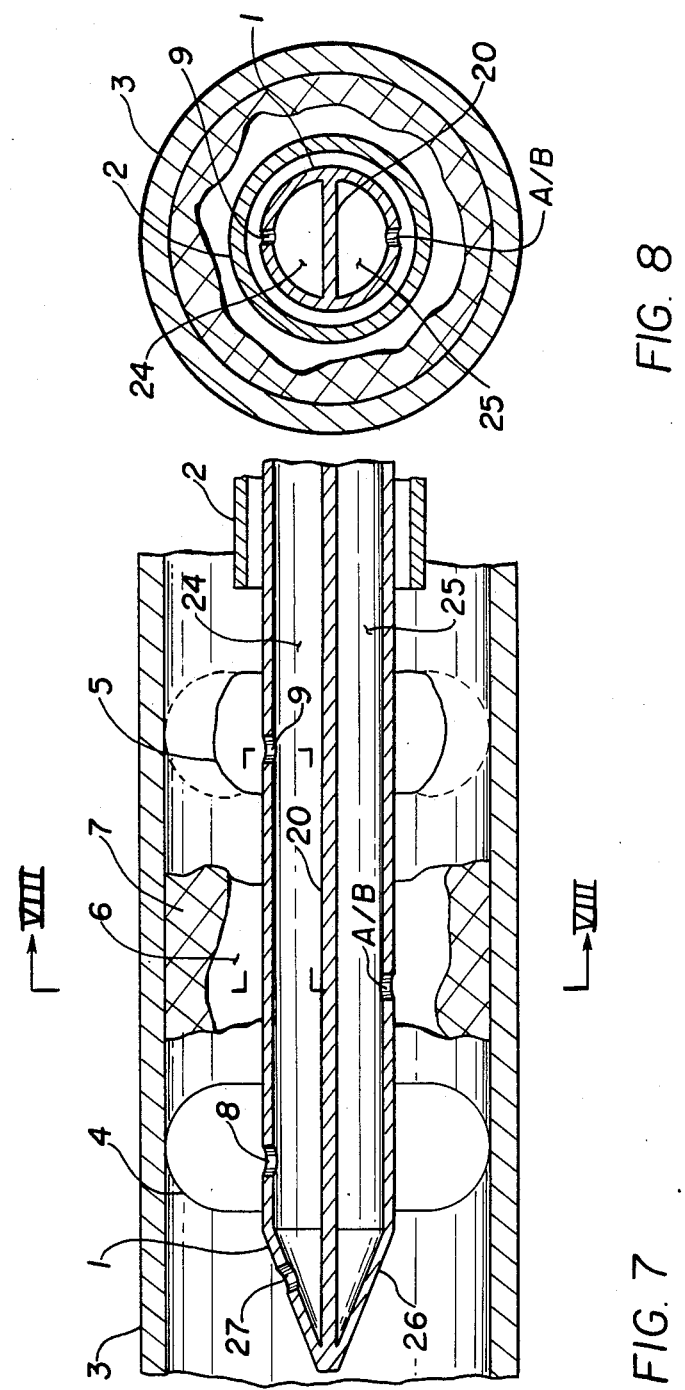

United States Patent [19]

Weikl et al.

[11] Patent Number: 4,610,662
[45] Date of Patent: Sep. 9, 1986

[54] METHOD FOR THE ELIMINATION OR THE ENLARGEMENT OF POINTS OF CONSTRICTION IN VESSELS CARRYING BODY FLUIDS

[75] Inventors: Andreas Weikl; Volkmar Merkel, both of Erlangen, Fed. Rep. of Germany

[73] Assignee: Schneider Medintag AG, Zurich, Switzerland

[21] Appl. No.: 517,069

[22] Filed: Jul. 22, 1983

[51] Int. Cl.$^4$ ............................................. A61M 25/00
[52] U.S. Cl. ..................................... 604/53; 604/101; 128/328; 128/348.1
[58] Field of Search ..................... 128/328, 344, 348.1; 604/101, 102, 53, 49-52, 54, 28, 265, 266, 269

[56] References Cited

U.S. PATENT DOCUMENTS

| | | | |
|---|---|---|---|
| 2,687,131 | 8/1954 | Raiche | 128/349 |
| 4,224,929 | 9/1980 | Furihata | 128/6 X |
| 4,271,839 | 6/1981 | Fogarty et al. | 128/344 |
| 4,430,083 | 2/1984 | Ganz et al. | 604/265 X |

FOREIGN PATENT DOCUMENTS

| | | |
|---|---|---|
| 1069823 | 11/1959 | Fed. Rep. of Germany . |
| 2816391 | 11/1978 | Fed. Rep. of Germany . |
| 2848484 | 5/1979 | Fed. Rep. of Germany . |
| 2834956 | 2/1980 | Fed. Rep. of Germany . |
| 2933266 | 5/1981 | Fed. Rep. of Germany . |
| 1460776 | 10/1966 | France ............................... 128/328 |
| 2350849 | 9/1977 | France . |
| 2054385 | 2/1981 | United Kingdom . |

*Primary Examiner*—Michael H. Thaler
*Attorney, Agent, or Firm*—Webb, Burden, Robinson & Webb

[57] ABSTRACT

For the provision of an apparatus to lessen or remove points of constriction in vessels of all types whereby ruptures and tears are to be avoided in the vessel walls and, during the treatment of stenosis in blood vessels, the danger of infarction is to be avoided, through use of a treatment catheter (1) that is equipped with two expandable balloons (4, 5) which seal off both sides of a point of constriction (6) in a vessel, whereby the degree of expansion of both balloons (4, 5) can be controlled externally, it is proposed that there be mounted in the wall of the treatment catheter (1) within the region confined by the balloons (4, 5) an inlet piece (A) for the supply of media capable of dissolving or crumbling into smaller particles the material (7) at the point of constriction and an outlet piece (B) for the removal of the material (7) dissolved or crumbled at the point of constriction, whereby these pieces are connected with an externally accessible conduit (10, 11) (FIG. 1).

10 Claims, 11 Drawing Figures

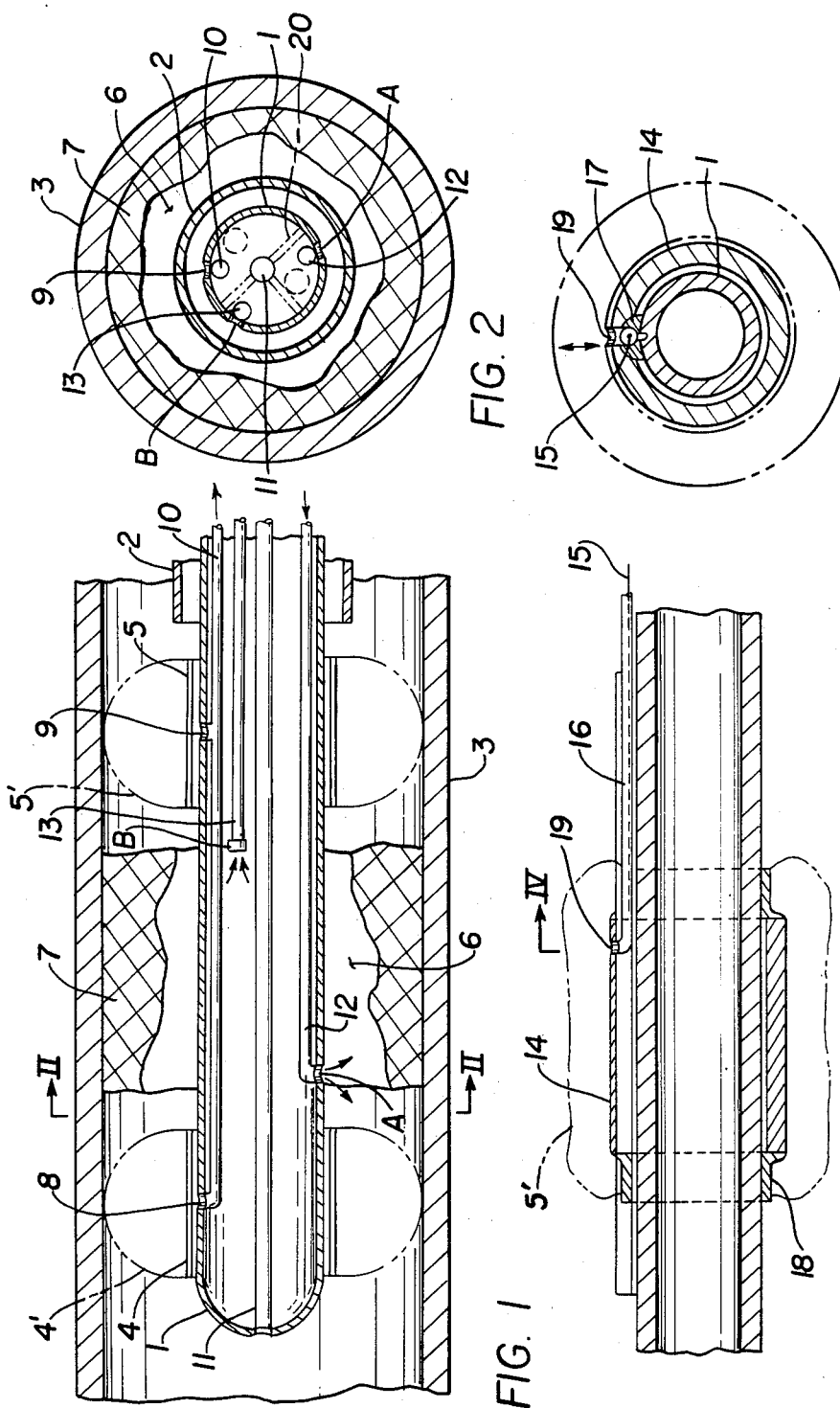

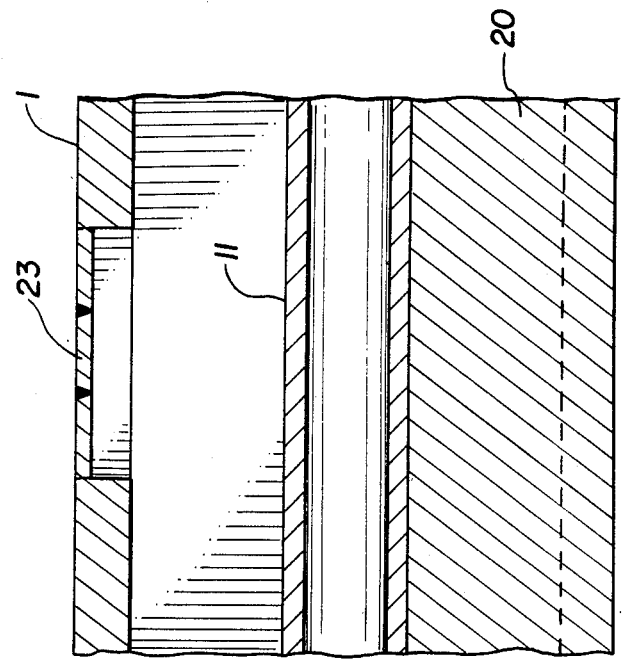
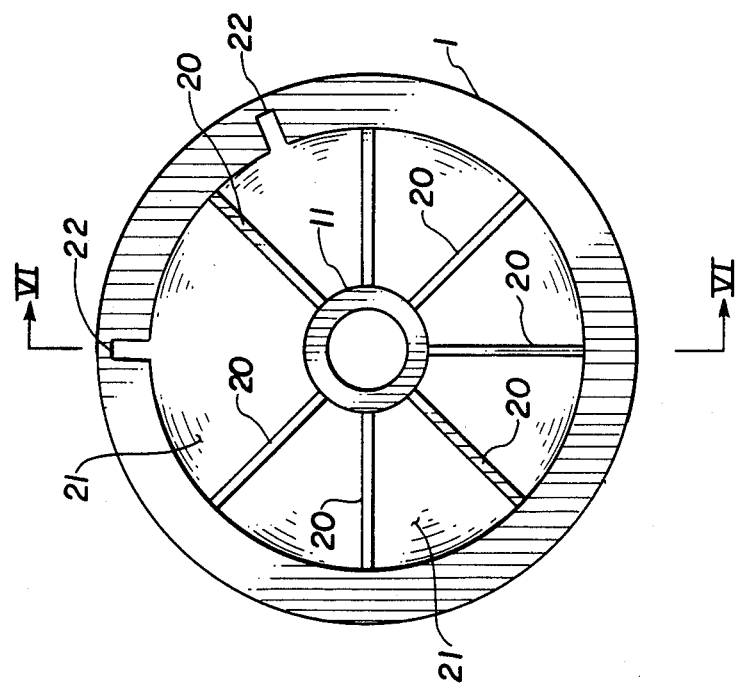
FIG. 6
FIG. 5

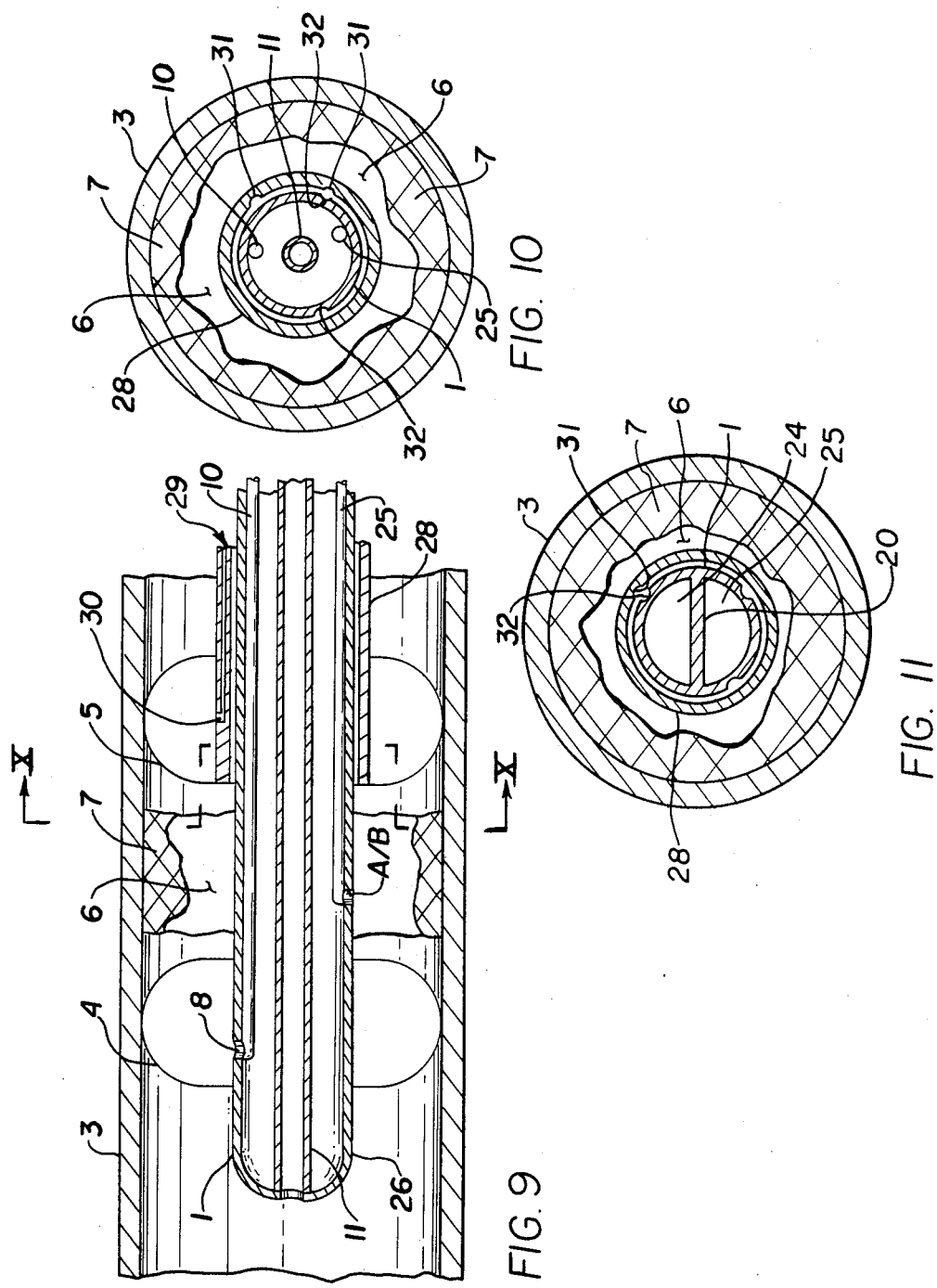

METHOD FOR THE ELIMINATION OR THE ENLARGEMENT OF POINTS OF CONSTRICTION IN VESSELS CARRYING BODY FLUIDS

The invention relates to an apparatus and method for the elimination or the enlargement of points of constriction in vessels carrying body fluids.

An apparatus of this art known from DE-AS No. 10 69 823 has as least two expandable balloons arranged one behind the other and separated by a given distance from each other on the vascular end of a treatment catheter. Each balloon is connected with an externally accessible conduit and can be inflated separately be external pressure. After insertion of the treatment catheter into a ureter, the ureter can be distended by inflating the balloons. A concretion which gives rise to a point of constriction or which can block the ureter can be confined between the balloons. While the balloons are in expanded condition the treatment catheter can be withdrawn from the ureter and thus remove the concretion. However, such a process can lead to complications when the concretion, for example, becomes wedged during withdrawal between a balloon and the inner wall of the ureter. By changing the expansion of the balloons the concretion must be correctly reconfined within the region bounded by the balloons. Upon such withdrawal the entire ureter from the narrow point on is subjected to a pronounced distention and the inner wall is especially stressed by the strong frictional pressure. Thus the pressure can result in tearing and separation of at least the inner wall of the ureter.

Furthermore, it is already understood from DE-OS No. 30 28 089 for the enlargement of points of constriction in the arterial system to use a treatment catheter on the end of which is fixed a balloon whose circumference can be expanded by a determined amount. This balloon is situated in the region of the point of constriction and is filled by a catheter with fluid such that the tissue in the blood vessel wall which is causing the point of constriction is compressed and remains in that condition. In the course of this procedure there are not many means for avoiding tearing the intima—the innermost wall of the vascular system—during the dilation. Moreover, there exists the danger that the interior vascular layers will be partially separated and cover the open interior space of the blood vessel which can lead to obstructions in the vascular system and/or reduced blood flow to those organs which are supplied by the afflicted blood vessel. Thus, for example, insufficient blood supply to the coronary arteries can give rise to an infarct.

The requirements to be met by the present invention consist of the provision of a reliable, economically producible apparatus of simple design with the aid of which the points of constriction of vessels that carry any given body fluid, irrespective of their spatial arrangement or extension in the vascular system, are reduced or eliminated to such an extent that no collapses or tears in the vascular walls can occur. Upon application in the blood vessels of an apparatus in accordance with the invention, provision of the organ or organs located behind the point of constriction is assured even during a longer treatment period for the point of constriction, and consequently even in these cases the danger of infarction is precluded.

These requirements are met in accordance with the invention.

By establishing a gap between the two balloons and its connection to an externally accessible conduit, any point of constriction can be gently removed in a relatively short time by targeted dissolution or crumbling of material at the point of constriction. In this procedure virtually no unfavorable side effects occur as a result of the distension of the vessel since this distension is undertaken in a healthy region of the vessel and only at two closely bounded points. The apparatus in accordance with the invention can therefore be used in all of those cases where the point of constriction is formed by substances that can be dissolved and/or crumbled into smaller pieces.

By softening the material at the point of constriction, the removal of same from the vicinity of the point of constriction is particularly unproblematic since the danger of damaging the vessel walls is totally precluded in this case due to the consistency of the material at the point of constriction.

As a result of a favorable configuration of the invention, a supply conduit can also be provided through which sufficient support for the organ located behind the treatment area can be assured simultaneously with treatment of the point of constriction. It is especially advantageous that, by use of this invention within predictable regions of vessels carrying body fluids, treatment fluids in a definable range, even in rather strongly concentrated form, can be brought to act upon material at the point of constriction for quite arbitrarily selectable time intervals.

Favorable configurations of the invention are the subject of the subordinate claims.

There follows a more detailed explanation of the invention by way of illustrative examples which are presented in the drawing in greatly expanded scale. There is shown:

FIG. 1 In longitudinal cross-section, a blood vessel with inserted guidance and treatment catheters as well as confinement balloons situated on both sides of the point of contracted passage, FIG. 2 a cross-section as defined by the intersecting line II—II of FIG. 1, FIG. 3 a longitudinal section of the treatment catheter with a movable balloon mounted on it, FIG. 4 a cross-section as defined by the intersecting line IV—IV FIG. 3, FIG. 5 a view of a treatment catheter with retracted partitions for the formation of conduits to feed and to drain liquids or gases, FIG. 6 A longitudinal section of a part of a treatment catheter with partially perforated lateral surfaces or predetermined points of rupture, as defined by the intersecting line VI—VI of FIG. 5, FIG. 7 a longitudinal view of a section of a vessel with inserted treatment and guidance catheters and with a conduit, which provides support and simultaneously supplies the balloon with pressure, in the treatment catheter, FIG. 8 a cross-section as defined by the intersecting line VIII—VIII of FIG. 7, FIG. 9 a longitudinal view of a section of a blood vessel with inserted treatment catheter upon which is mounted a movable catheter used for confining the region in question, FIG. 10 a cross-section as defined by the intersecting line X—X of FIG. 9 and FIG. 11 a cross-section corresponding to an intersection line X—X of FIG. 9, but with a treatment catheter with only one longitudinal partition, as is shown in FIGS. 7 and 8.

The treatment catheter 1 is inserted by a guidance catheter 2 into a blood vessel 3. It extends beyond the guidance catheter 2 so far that the balloons 4 and 5 positioned on the treatment catheter 1, along with the point of constriction 6 or stenosis which is confined between them, lies in front of the end of the guidance catheter 2. The point of constriction 6 is usually formed from a spongy, fatty, calcium-rich tissue 7 which is indicated by cross-hatching in the drawing. In cases where the tissue 7 completely or almost completely closes off the blood flow of the blood vessel 3, the treatment catheter 1 or tentatively another instrument is pushed through the latter. Otherwise, the treatment catheter 1 is brought far enough through the remaining opening at the point of constriction 6 that the balloon 4 in its inflated condition 4' seals off the point of constriction 6 to the rear and the balloon 5 in its inflated condition 5' seals off the point of constriction 6 to the front side, i.e. that the blood vessel 3 is totally closed off on both sides of the point of constriction 6.

The expansion or inflation of the balloons 4, 5 can be accomplished by a gas or liquid medium. The letter can be let in or out across the inlet/outlet nozzle 8 or 9 through an externally connected, pressurized conduit, by which means the quantity and pressure can be regulated. In order to assure during the treatment of points of constriction 6 in blood vessels the support of the organ or organs behind the point of constriction 6 despite the seals at both sides of the latter, especially in cases of rather long operating times, an additional support conduit 11 is provided which represents a type of "bypass line" to the sealed off area around the point of constriction. The support conduit 11 is preferably arranged coaxially with the treatment catheter 1. It can, however, in deviating from the described manner, also be installed or connected in another position and/or in the form of a rather large number of conduits. Through this support conduit 11 blood and/or another liquid can be introduced in front of the blockage from the outside, preferentially under positive pressure, or from the blood steam with the help of an overflow conduit. These means provide sufficient operating times without giving rise to a danger of infarction.

In order that only the fatty, calcium-rich tissue 7 of the point of constriction 6 is affected and not the inner layers of the blood vessel 3, a chemical medium in the form of a solution, which is capable of dissolving the tissue 7, is pumped through the supply conduit 12 with the inlet piece A into the space containing the tissue 7 of the point of constriction. For this purpose digestive enzymes and similar substances are suitable, among other possibilities.

For other applications, such as the treatment of gall or kidney concretions, still other substances such as solvent acids can be considered.

For the removal of dissolved or crumbled particles and for reducing the treatment time, it is advantageous to have a continuous, circulating rinse process which is assured by a return conduit 13 with the outlet piece B. In principle, however, it is also possible to return through a single conduit the medium which dissolves or crumbles the tissue 7 at the point of constriction and alternately to drain the dissolved or crumbled tissue 7 at the point of constriction through the same conduit. Such a development is shown in FIGS. 7, 8 and 11 which are to be explained in greater detail later. It is evident that the feed conduit 12 can also be used a a return conduit, and that the return conduit 13 can also be used as a feed conduit. The number of feed and return conduits can also always be increased according to need. The same number of inlet/outlet nozzles 8, 9 or openings in the treatment catheter 1 may be chosen as there are inlet and runback channels so that an opening can be assigned to each channel.

In order to be able to accommodate the extent of the blockage as determined by the extension of the tissue 7, it is advantageous not to mount the balloon 5 rigidly—as shown in FIG. 1—but rather movably on the treatment catheter 1. One such design is represented in FIGS. 3 and 4. The balloon is thereby fixed to a sliding member 14 which can be moved from the outside back and forth, preferably with the aid of a rather stiff strand 15 of synthetic fiber—preferentially of Perlon or equal. The artificial fiber strand 15 can thereby pass through a conduit 16 which is incorporated, for example, in the elongated projection 17, of the treatment catheter 1 that also serves simultaneously to guide the sliding member 14, and which thus is practically incorporated into the reinforcement of the wall of the projection. Simultaneously, the inflation medium can be introduced and removed through this conduit 16 and its pressure can be regulated externally.

In order that the gap between sliding member 14 and the outer wall of the treatment catheter 1 can be faultlessly sealed, there is provided, at least on the side facing the point of constriction 6, a sealing sleeve 18 which additionally contributes to effective sealing at this point because of its particular shape. The orifice, through which the gaseous or liquid expansion medium is supplied or removed for the expansion of the now movable balloon 5, is identified as 19.

Instead of tubular conduits 10, 12, 13 which are positioned and mounted on the wall sections of the treatment catheter 1, the inner cavity of the treatment catheter 1 can also be accordingly subdivided by longitudinal partitions 20 (FIGS. 2 and 5) such that chambers 21 are established through which, depending upon the requirements, the corresponding medium can be fed.

Furthermore, in many cases—especially when using longitudinal partitions 20—instead of mounting inlet/outlet orifices 8 and 9 or orifices A and B at the ends of the conduits 12 and 13, it can be advantageous at these points to provide the walls of the treatment catheter 1 with perforations 23 so that the latter appear, as can be seen in FIGS. 5 and 6, only after breaking the predetermined points of rupture 22, thus allowing the length of the perforated section of the catheter to be adjusted, just before the operation, in accordance with the size of the region of constriction which is to be treated.

FIGS. 7 and 8 present a further illustrative example in accordance with the invention with a single longitudinal partition 20. The treatment catheter 1 is thereby divided into two conduits of which the one is configured as a combined pressure and support conduit 24 and the other as a combined feed and drain conduit 25 for the point of constriction 6. The one conduit 24 has an orifice 8 or 9 in the region of each balloon 4, 5 and an outlet orifice 27 on the vascular end 26 of the treatment catheter 1. The other conduit 25 has an inlet/outlet orifice A/B in the region of confinement. Through use of this treatment catheter 1, whose potentially small diameter is especially well suited for vessels with small cross-sections, it is possible to expand simultaneously the balloons 4, 5 by means of the fluid pressure generated in conduit 24 by an externally supplied fluid, in particular, a support fluid for organs located downstream—e.g., blood—and consequently to seal on both sides the confined region around the point of constriction 6. The fluid is then discharged under pressure through the outlet orifice 27. On the other hand, the substance for dissolving the material at the point of constriction, or another type of substance, can be continuously or periodically pumped through the other conduit 25 into the point of constricted passage 6 and subsequently the dissolved material can be drained from the point of constriction along with the remaining substance. Thus the process provides the desired effect through use of an easily manufactured treatment catheter 1, while maintaining a very small diameter of this catheter.

In accordance with a further, advantageous development of the invention, either balloon 4 or 5 can be equipped in this configuration with a covering or wall which is more elastic than that of the other balloon. In the example shown in FIGS. 7 and 8, this balloon is 4. It is thus possible to establish and regulate the pressure such that both balloons 4 and 5 do seal and, for example, balloon 4 continues to seal during withdrawal of the substances from the confined region but balloon 5 does not (see FIG. 7). Hereby, it is possible to use in addition the guidance catheter 2 for rinsing or draining since, with such a pressure setting, the point of constriction 6 is also externally accessible from the side of the guidance catheter 2.

For practical considerations the balloons 4, 5 of the apparatus in accordance with the invention can be configured such that they assume a definite form and size and then do not expand further, even upon application of considerably higher pressure.

In the advantageous configurations of the object of the invention which are shown in FIGS. 9, 10 and 11, the balloon 5, which is rather far from the vascular end 26 of the treatment catheter 1, is situated on or at the end of a region-confining, or confinement, catheter 28 which is mounted on the treatment catheter 1 by a sliding attachment. The confinement catheter 28 is equipped with a pressure conduit 29 which preferably is integrated into the wall of the confinement catheter 28, the length of the confined region can be chosen according to requirements and can be sealed off or opened by means of the separate expansion capability of the balloon 5. Here again a space can advantageously be retained between the treatment catheter 1 and the confinement catheter 28, and the latter can be used for rinsing or removing fluid. For a very compact design, one or more indentations 31 can be provided on the inner wall of the confinement catheter 28 and/or indentations 32 on the outer wall of the treatment catheter 1, as shown in FIGS. 10 and 11. In order to subsequently achieve greater flow cross-sections, the indentations 31 of the confinement catheter 28 can be positioned opposite the indentations 32 of the treatment catheter 1. Even with this design solution, a single longitudinal partition—as shown in FIG. 11—can be provided in the treatment catheter 1, and the treatment catheter 1 can include orifices, as demonstrated by FIG. 7, so that it is additionally possible to attain the beneficial effects indicated there. Furthermore, the apparatuses as shown in FIGS. 9, 10 and 11 can include a guidance catheter 2 which is not illustrated.

The catheter for the treatment of points of constriction, in accordance with the invention, can be used with all types of vessels carrying body fluids, thus with all types of blood vessels or other fluid-bearing vessels, such as conduits carrying medicinal liquids, or also with larger lymphatic vessels.

Further areas of application—besides the primary area of treating points of constriction in blood vessels—are, for example, the treatment of constrictions in the bile duct, in the outlet duct of the pancreas, or in the spinal canal.

It is also possible with the invention to feed chemical substances in high or rather high concentrations to regions of vessels for the purpose of stimulating capillary branching from these vascular regions outwards. Of special interest in this regard are the materials described by Dr. Josef Wissler, Max-Planck-Institut, Bad Nauheim, for the stimulation of vascular branching, angiotropines by name, which are isolated from white blood corpuscles.

The treatment of points of constriction with the catheter in accordance with the invention can be undertaken in several steps and, if necessary, with the use of various treatment media and/or various concentrations of the treatment media.

We claim:

1. A method of treating stenosis by eliminating or expanding the points of constriction which are customarily formed of a sponge-like calcified and fatty tissue in blood carrying vessels of the body through use of a flexible treatment catheter having separate support conduits formed by longitudinal partition walls and at whose end two balloons are situated, said method comprising the steps of sealing off the section of the blood vessel containing the stenosis with the two balloons, introducing a solvent of predetermined concentration and duration of effect to act upon the stenosis through a first support conduit in the catheter such that the tissue of the stenosis is dissolved, softened, or crumbled into smaller particles, and draining the particles from the sealed section of the blood vessel through a second separate support conduit.

2. The method defined in claim 1, and including maintaining the circulation of blood contained in the blood-carrying vessels to the downstream organs by a further separate support conduit in the catheter.

3. The method defined in claim 1, wherein the solvent, as determined by its type, concentration, and duration of effect, acts upon the stenosis only to soften the tissue to permit it to be removed as a whole by the treatment catheter when the treatment catheter is withdrawn from the vessel.

4. The method defined in claim 1, wherein the solvent, as determined by its type, concentration, and duration of effect, acts upon the stenosis to such an extent that the tissue of the stenosis is crumbled into smaller particles which are removed through the second separate draining support conduit of the treatment catheter.

5. The method defined in claim 1, wherein the solvents are selected from the group consisting of enzymes, acids and alkaline solutions.

6. The method defined in claim 5, wherein the acid is a nitrous acid.

7. The method defined in claim 5, wherein the alkaline solution is caustic soda.

8. The method defined in claim 1, characterized in that the duration of effect of the solvent on the stenosis is limited to a predetermined time interval by inhibitors.

9. The method defined in claim 1, and including a circulating rinse for the removal of the tissue at the point of constriction which has been dissolved, softened or crumbled into smaller particles.

10. The method defined in claim 9, characterized in that the double-balloon catheter is used for performing the circulating rinse process.

* * * * *

UNITED STATES PATENT AND TRADEMARK OFFICE
CERTIFICATE OF CORRECTION

PATENT NO. : 4,610,662

DATED : September 9, 1986

INVENTOR(S) : Andreas Weikl et al.

It is certified that error appears in the above-identified patent and that said Letters Patent is hereby corrected as shown below:

After the line listing the filing date insert the following:

--Foreign Application Priority Data

PCT/CH82/00122, filed Nov. 23, 1982--.

Column 1 Line 14 "be" (second occurrence) should read --by--.

Column 1 Line 31 "pressure" should read --process--.

Column 1 Line 44 "for" should read --of--.

Column 2 Line 5 After "constriction" insert --and one or more subsequent rinsing processes of the point of constriction--.

Column 3 Line 24 "letter" should read --latter--.

Column 4 Line 1 "a" (first occurrence) should read --as--.

Signed and Sealed this

Sixth Day of January, 1987

Attest:

DONALD J. QUIGG

Attesting Officer

Commissioner of Patents and Trademarks